United States Patent [19]

Linder et al.

[11] Patent Number: 5,183,653
[45] Date of Patent: Feb. 2, 1993

[54] BORONIC ACID ADDUCTS OF METAL DIOXIME COMPLEXES USEFUL IN LABELLING PROTEINS AND OTHER AMINE-CONTAINING COMPOUNDS

[75] Inventors: Karen E. Linder, Highland Park; Adrian D. Nunn, Ringoes; Kondareddiar Ramalingam, North Brunswick, all of N.J.

[73] Assignee: E. R. Squibb & Sons, Inc., Princeton, N.J.

[21] Appl. No.: 508,433

[22] Filed: Apr. 13, 1990

[51] Int. Cl.⁵ .................... A61K 49/02; A61K 43/00
[52] U.S. Cl. ...................................... 424/1.1; 534/10; 534/14; 530/391.5
[58] Field of Search ............... 424/1.1, 85.91; 534/10, 534/14; 530/389, 391, 402, 409, 391.5; 556/37, 45

[56] References Cited

U.S. PATENT DOCUMENTS

| | | | |
|---|---|---|---|
| 4,705,849 | 11/1987 | Nunn et al. | 424/1.1 X |
| 4,871,836 | 10/1989 | Francesconi et al. | 534/10 |

FOREIGN PATENT DOCUMENTS

| | | | |
|---|---|---|---|
| 0237150 | 9/1987 | European Pat. Off. | 424/1.1 |
| 0247866 | 12/1987 | European Pat. Off. | 424/1.1 |
| 0271806 | 6/1988 | European Pat. Off. | 424/1.1 |
| WO87/05030 | 2/1987 | PCT Int'l Appl. | 424/1.1 |

OTHER PUBLICATIONS

W. C. Eckelman et al., "Comparison of Tc-99m and In-111 labeling of conjugated antibodies", Nucl. Med. Biol., 13, 335-343 (1986).
Jurisson et al., Inorg. Chem., 1991, 30, 1820-1827.
E. Deutsch et al., "Technetium Chemistry and Technetium Radiopharmaceuticals", Prog. Inorg. Chem., 30, 75-139, (1983).
C. H. Paik et al., "Transchelation of $^{99m}$Tc from low affinity to high affinity sites of antibody", Nucl. Med. Biol., 13, 359-362 (1986).
A. L. Jones et al., "Radiolabeling of Monoclonal Antibody (MAb) fragments with Technetium-99m (Tc-99m) using a One Vial Kit", J. Nucl. Med., 31, 905 (1990).
K. Y. Pak et al., "Stability and Immunoreactivity of Technetium-99m Antibody Fragments by a Direct Labeling Method", J. Nucl. Med., 31, 905 (1990).
A. R. Fritzberg et al., "Specific and stable labeling of antibodies with technetium-99m with a diamide dithiolate chelating agent", Proc. Natl. Acad. Sci., 85, 4024-4029 (1988).
J. Franz et al., "The production of Tc-99m labeled conjugated antibodies using a cyclam based bifunctional chelating agent", Nucl. Med. Biol., 26, 293-299 (1987).
J. R. Morphy et al., "Antibody Labelling with Functionalised Cyclam Macrocycles", J. Chem. Soc. Chem. Commun., 156-158, (1988).
Y. Arano et al., "Synthesis and Evaluation of a New Bifunctional Chelating Agent for 99m-Tc Labeling Proteins: p-Carboxyethylphenylglyoxaldi(N-methylthiosemicarbazone)", Nucl. Med. Biol, 12, 425-430 (1986).
Y. Arano, et al., "Technetium-99m-Labeled Monoclonal Antibody with Preserved Immunoreactivity and High In Vivo Stability", J. Nucl. Med., 28, 1027-1033 (1987).
E. F. Byrne et al., "Technetium-99m bifunctional chelating agent-thiolactone coupling to biomolecules. N₂S₂ ligand for chelation to Technetium", J. Nucl. Med., 24, p. 126 (1983).
S. Z. Lever et al., "Synthesis of a novel bifunctional chelate designed for labeling proteins with Technetium-99m", Tetrahedron Lett., 29, 3219-3222 (1988).
H. K. Misra et al., "Synthesis of a Novel Diaminodithiol Ligand for Labeling Proteins and Small Molecules with Technetium-99m", Tetrahedron Lett., 30, 1885-1888 (1989).
K. E. Baidoo et al., "Synthesis of a Diaminedithiol Bifunctional Chelating Agent for Incorporation of Technetium-99m into Biomolecules", Bioconjugate Chem., 1, 132-137 (1990).
M. M. Morelock et al., "Metallothionein: A Bifunctional Chelator for the Radiolabeling of Biologically Active Molecules", Experientia, 52 (Supplement: Metallothionein II), 247-253 (1987).
M. M. Morelock et al., "Technetium Metallothioneins", Inorg. Chem., 27, 3137-3140 (1988).
B. A. Brown et al., "Conjugation of Metallothionein to a Murine Monoclonal Antibody", Anal. Biochem., 172, 22-28 (1988).
A. R. Fritzberg, "Advances in $^{99m}$Tc-labeling of antibodies", Nuklearmedizin, 26 7-12 (1987).
A. R. Fritzberg et al., "Radiolabeling of antibodies with $^{99m}$Tc using N₂S₂ ligands", J. Nucl. Med., 27, 957-958 (1986).
D. Wilkening et al., "Tc-99m Antibody Labeling with N₃S and N₂S₂ Amide Mercaptides: Active Ester Complex Yield and Slide Chain Length", J. Nucl. Med., 29, 815 (1988).
J. R. Morphy et al., "Antibody labeling with Functionalised Cyclam Molecules", J. Chem. Soc. Chem. Commun., 156-158 (1988).
S. Mirzadeh et al., "Radiometal Labeling of Immunoproteins: Covalent Linkage of 2-(4-Isothiocyanatobenzyl)diethylenetriaminepentaacetic Acid Ligands to Immunoglobulin", Bioconjugate Chem., 1, 59-65 (1990).

Primary Examiner—Robert L. Stoll
Assistant Examiner—John M. Covert
Attorney, Agent, or Firm—Theodore R. Furman, Jr.

[57] ABSTRACT

Boronic acid adducts of metal dioxime complexes are useful as reagents for labeling proteins and other amine-containing compounds.

32 Claims, No Drawings

BORONIC ACID ADDUCTS OF METAL DIOXIME COMPLEXES USEFUL IN LABELLING PROTEINS AND OTHER AMINE-CONTAINING COMPOUNDS

BRIEF DESCRIPTION OF THE INVENTION

Boronic acid adducts of metal dioxime complexes having the formula $$MX(Y)_3Z \qquad \text{I.}$$

are useful as amine and protein labeling reagents. In formula I, and throughout the specification, the symbols are as defined below:

M is an isotope of technetium or rhenium;
X is an anion;
Y is a vicinal dioxime having the formula

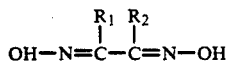

$$\text{II.}$$

wherein $R_1$ and $R_2$ are each independently hydrogen, halogen, alkyl, aryl or a 5 or 6 membered nitrogen, sulfur or oxygen containing heterocycle, or taken together $R_1$ and $R_2$ are $-(CR_8R_9)_n-$ wherein n is 3, 4, 5 or 6 and $R_8$ and $R_9$ are each independently hydrogen or alkyl.

Z is a boron derivative having the formula $$B-(A_1)_p-E \qquad \text{III.}$$

wherein E is an aromatic or non-aromatic moiety which contains a protein reactive functional group or a functional group which can readily be converted to a protein reactive functional group. E may optionally contain a water-solubilizing functional group.

Examples of the moiety "E" include aromatic groups of the formula

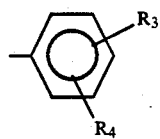

$$\text{IV}$$

and non aromatic groups of the formula

$$\text{V}$$

where $R_5$ is hydrogen or alkyl, and $R_3$ is a functional group that is capable of reacting with an amino group to form a covalent bond. Examples of suitable groups for $R_3$ include N=C=S, N=C=O, acyl halide derivatives, activated esters, N-hydroxysuccinamide derivatives, or an alkyl halide group. The isothiocyanate group (N=C=S) is preferred.

$R_4$ is either hydrogen or a water solubilizing functionality such as COOH, carboxylalkyl, hydroxyalkyl, $SO_2H$, alkyl sulfonate, sulphonamide, hydroxyl or a pharmaceutically acceptable salt thereof.

If the moiety "E" is aromatic, $R_4$ may be ortho, meta or para to $R_3$. It is preferred that $R_4$ is in a meta position in relationship to both $R_3$ and the spacer group $(A_1)p$.

$(A_1)$ in the boron derivatives of formula III can be any chemical moiety which can serve to distance or otherwise isolate the moiety represented by "E" from the rest of the complex of formula I. For example, wherein p is an integer greater than zero, $A_1$, or the various A units that form a straight or branched chain are independently selected from $-CH_2-$, $-CHR_6-$, $-CR_6R_{10}-$, $-CH=CH-$, $-CH=CR_{11}-$, $-CR_6=CR_{12}-$, $-C\equiv C-$, cycloalkyl, cycloalkenyl, aryl, heterocyclo, oxygen, sulfur,

$-HC=N-$, $-CR_6=N-$, $-NR_6-$, wherein $R_6$, $R_{10}$, $R_{11}$ and $R_{12}$ are independently selected from alkyl, alkenyl, alkoxy, aryl, 5- or 6-membered nitrogen containing heterocycle, halogen, hydroxy or hydroxyalkyl.

In the complexes of the present invention the preferred moieties for $(A_1)p$ are alkyl, aryl, oxa-alkyl, hydroxyalkyl, hydroxyalkoxy, carboxylalkyl, arylalkyl, arylalkylamide, alkylamide and alkylsulfonate.

p may be zero or an integer from one to one hundred with zero to twenty being the preferred range. Preferred boron derivatives of this invention represented by include

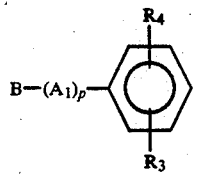

wherein p is zero to six, $R_3$ is a functional group that is capable of reacting with an amino group to form a covalent bond, and $R_4$ is hydrogen or a solubilizing functionality as defined previously.

The most preferred values for the boron derivative Z are compounds of the formula

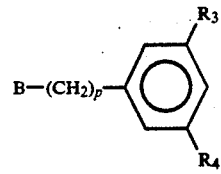

$$\text{VI.}$$

wherein p is zero or one, $R_3$ is isothiocyanate and $R_4$ is hydrogen or a water solubilizing functionality such as COOH, carboxylalkyl, hydroxyalkyl, $SO_3H$, alkyl sulfonate, sulphonamide or hydroxyl.

The term anion refers to any chemical entity which bears a negative charge. Exemplary groups are $Cl^\ominus$, $Br^\ominus$, $F^\ominus$, $I^\ominus$, $OH^\ominus$, $SR^\ominus$, $S-C\equiv N^\ominus$ and $N=C=S^\ominus$. The preferred anionic moieties are $Cl^\ominus$ and $OH^\ominus$.

Listed below are definitions of the terms used to describe the complexes of this invention. These definitions apply to the terms as they are used throughout the specification (unless they are otherwise limited in specific instances) either individually or as part of a larger group.

The term "alkyl" refer to both straight and branched chain groups. Groups having 1 to 10 carbon atoms are preferred.

The term "aryl" refers to phenyl and substituted phenyl. Preferred are phenyl and phenyl substituted with 1, 2 or 3 alkyl, haloalkyl, dialkylaminoalkyl, alkoxy, alkoxyalkyl, halogen, hydroxy, or formyl groups.

The expression "5 or 6-membered nitrogen containing heterocycle" refers to all 5 and 6-membered rings containing at least one nitrogen atom. Exemplary aliphatic groups are dehydro derivatives of a compound having the formula

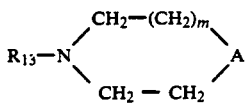

wherein m is 0 or 1 and A is oxygen, sulfur, N—$R_{13}$ or CH—$R_{14}$, wherein R a is alkyl, aryl, or arylalkyl and $R_{14}$ is hydrogen, alkyl, aryl or aryl alkyl. Also included within the expression "5 or 6-membered nitrogen containing heterocycle" are aromatic groups. Exemplary heteroaromatic groups are pyrrolyl, imidazolyl, oxazolyl, pyrazolyl, pyridinyl, and pyrimidinyl groups. The above groups can be linked via a hetero atom or a carbon atom.

The expression "5 or 6-membered nitrogen or oxygen containing heterocycle" refers to all 5 and 6-membered rings containing at least one nitrogen, sulfur or oxygen atom. Exemplary groups are those described above under the definition of the expression "5 or 6-membered nitrogen containing heterocycle". Additional exemplary groups are 1,4-dioxanyl, furanyl and thiophenyl.

It should be understood that the various moieties in ($A_1$)p, or $R_1$ and $R_2$ of the vicinal dioxime should not contain functional groups that will react with the $R_3$ group on the boron derivatives of formula III or IV.

DETAILED DESCRIPTION OF THE INVENTION

Preparation of the technetium complexes of this invention can best be accomplished using technetium-99m in the form of the pertechnetate ion. The pertechnetate ion can be obtained from commercially available technetium-99m parent-daughter generators; such technetium is in the +7 oxidation state. The generation of the pertechnetate ion using this type of generator is well known in the art, and is described in more detail in U.S. Pat. No(s). 3,369,121 and 3,920,995. These generators are usually eluted with saline solution and the pertechnetate ion is obtained as the sodium salt.

Preparation of the complexes of this invention wherein M is an isotope of rhenium can best be accomplished using rhenium in the plus 3, plus 4, plus 5 or plus 7 oxidation state. Examples of compounds in which rhenium is available in the plus 3 oxidation state are $ReCl_3(CH_3CN)(PPh_3)_2$ and $[Re_2Cl_8](NBu_4)_2$ wherein Ph=phenyl and Bu=butyl. Re(IV) is available as $K_2ReCl_6$ and Re(VII) is available as $NH_4ReO_4$ or $KReO_4$. Re(V) is available as $[ReOCl_4](NBu_4)$ and $[ReOCl_4](AsPh_4)$ and as $ReOCl_3(PPh_3)_2$ and as $ReO_2(pyridine)_4^\oplus$. Other Re(III), Re(IV), Re(V), Re(VII) reagents known to those skilled in the art can also be used.

To prepare the complexes of this invention requires a source of the metal ion as described above which is combined with a source of anion, a boronic acid derivative having the formula

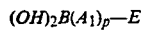   VII.

and a dioxime of formula II or a pharmaceutically acceptable salt thereof.

Alternatively, the complexes of this invention can be prepared by the reaction of a boronic acid derivative of formula VII with a compound of the formula MX(dioxime)$_3$. U.S. Pat. No. 4,714,605 discloses the compound MX(dioxime)$_3$ wherein M is technetium.

Complexes of the formula MX (dioxime)$_3$ wherein M is an isotope of rhenium can be prepared by combining a source of Re(III) such as $ReCl_3(CH_3CN)(PPh_3)_2$ or $[Re_2Cl_8](NBu_4)_2$ with a dioxime of formula II and a source of anion X. The formation of complexes ReX(dioxime)$_3$ proceeds when the mixture of Re(III) starting material, source of anion, and dioxime ligand of formula II are heated at 25°-100° C. for about 2 to 30 minutes at a pH of about one to about 4.

If the complexes of formula 1 are prepared from pertechnetate or perrhenate, the source of the anion moiety can be water or any compound or salt that dissociates to release an appropriate anion. Exemplary compounds include NaCl, NaBr and thiol containing compounds.

The formation of the complexes of formula I proceeds when the mixture of metal ion, source of anion, boronic acid derivative and dioxime is heated at about 25° C. to about 100° C. for about two to about 30 minutes. The preferred temperature is about 50° C. to about 100° C. and the preferred time of heating is from about two minutes to about 15 minutes. The optimal pH for the above reaction is from about one to about four.

If the source of technetium or rhenium is pertechnetate or perrhenate, or other starting material in an oxidation state higher than +3, the reaction mixture should also contain a reducing agent. Stannous ion is the preferred reducing agent, and can be introduced in the form of a stannous salt such as a stannous halide (e.g. stannous chloride or stannous fluoride). The reducing agent should be present in a concentration of about 1.5 micromolar to 6.6 millimolar.

Various complexing agents (also known in the art as chelating agents) can be included as part of the complexing reaction. The complexing agent should, of course, be pharmaceutically acceptable. Exemplary complexing agents are diethylenetriaminepentaacetic acid (DTPA), ethylene glycol-bis($\beta$aminoethyl ether)-N,N,N',N'-tetraacetic acid (EGTA), ethylenediamine tetraacetic acid (EDTA), citric acid, tartaric acid, malonic acid, etc.

The complexing reaction mixture can also include an accelerator (catalyst) which serves to improve the radiochemical purity (i.e., the per cent of the radioactivity that is in the desired chemical form) of the product. Exemplary accelerators are the $\alpha$-hydroxycarboxylic acids such as citric acid, tartaric acid, and malonic acid. A combination of DTPA and citric acid has been found to be preferred.

As it is necessary to prepare the complexes of this invention at, or near, the site where they are to be used, a kit having all of the components, other than the source of the technetium or rhenium, to prepare the boronic adducts of the metal dioxime complexes of formula I is an integral part of this invention. Such a kit contains a source of anion, a boronic acid derivative of formula VII (or compounds which can react in situ to form such a derivative), or a pharmaceutically acceptable salt thereof, a dioxime of formula II, or a pharmaceutically acceptable salt thereof, and a reducing agent. It may optionally contain complexing agent(s), accelerator(s), solubilization agents, and/or other components necessary to provide high radiochemical purity.

A multi-vial kit may also be used to prepare the complexes of this invention. For example, one vial of the kit could contain a source of anion, a dioxime ligand of formula II, or pharmacologically acceptable salt thereof, a reducing agent, and optional complexing agents. A source of technetium or rhenium is added to this kit, which is then heated to form the intermediate MX(dioxime)$_3$ (M=Tc,Re). The intermediate product from this kit is then added to a second vial that contains a boronic acid derivative of formula VII (or a compound which can react in situ to form such a derivative).

The kits of this invention can be formulated in aqueous solution. To optimize the stability of the kit, and to optimize the radiochemical purity of the labeled product, the pH of the kit should be adjusted to fall within the range of about 1.0 to 4.0 using a pharmaceutically acceptable acid or base (e.g., hydrochloric acid or sodium hydroxide). Preferably, the pH of the kit will be about 2.0. It is also preferred that the kit be in lyophilized form. While "wet" kits (i.e. kits which provide all components in solution) can be used, they are not as efficacious as the corresponding lyophilized kit.

The compounds of formula VII wherein R$_3$ is NCS are novel and form an integral part of this invention. These boronic acids or pharmaceutically acceptable salts thereof of formula VII are bifunctional reagents that will react with the above kit constituents to form the complexes of formula I. The reactive group R$_3$ will react with proteins or with other amine-containing compounds either before or after reaction with the metal M.

Working with the $^{99}$Technetium isotope, the structure of one of the complexes of this invention has been investigated and is believed to be

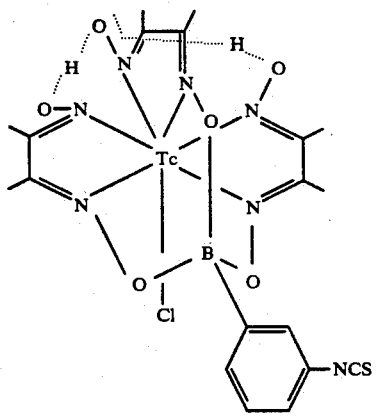

Coupling of the metal complexes of formula I, to proteins such as monoclonal and polyclonal antibodies, polypeptides such as albumin, insulin, hemoglobin and fibrinogen, hormones such as angiotensin, adrenalin, and amine containing steroid, derivatives, amino acids such as glycine and cysteine, drugs such as penicillamine and alkaloids, or other amine-containing compounds such as enzymes and whole cells occurs via reaction of the group R$_3$ on the boron derivative Z with primary or secondary amines on the protein or other amine-containing compounds. If R$_3$ is isothiocyanato (N=C=S), the resultant thiourea bond is chemically very stable. Thus, a stable covalent link is formed that attaches the metal dioxime complexes of formula I to the protein or other amine-containing compound. An example of this reaction is shown below.

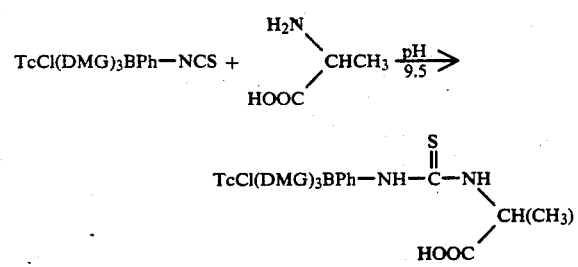

wherein DMG=Dimethylglyoxime.

It is also possible to form the complexes of formula I where the group Z on the boron cap is not initially a reactive functionality. This complex could then be converted, after the formation of the complex core, to another, more reactive compound, that contains a group Z that is reactive. For example, compounds that contain a boron cap Z such

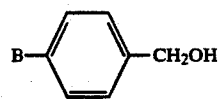

as can be converted, after formation, into active compounds that contain the boron cap

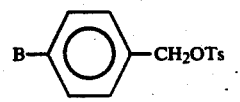

(Ts=tosyl). This activated compound could then be used for reaction with proteins.

Radiolabelled antibodies and antibody fragments are envisioned by this invention and are useful either as diagnostics or in radiotherapy. Antibody fragments include Fab, F(ab')$_2$, and Fab'. They are described by S. W. Burchiel et al. "Immunopharmokinetics of Radiolabeled Antibodies and their Fragments", Chapter 13 in "Tumor Imaging, The Radiochemical Detection of Cancer", editors S. W. Burchiel and B. A. Rhodes, Masson Publishing Inc., (1982). Uses of these radiolabeled antibodies and antibody fragments include the detection of clots and the diagnosis and treatment of cancer. Substrates such as drugs, proteins or hormones that are radiolabeled using the method described herein may be used to provide diagnostic anatomic images of organ systems, images of organ function, probes to biochemical processes and the diagnosis and treatment of cancer.

As described in further detail in the example section, it has been demonstrated that certain antibodies and antibody fragments labelled in the above-described manner retain their biological activity and hence are capable of localizing preferentially in tumors that express antigens that are recognized by a specific antibody. Because of this preferential localization of radiolabeled materials in tumors, antibodies and antibody fragments labelled in the manner described in this invention are useful in the diagnosis or therapy of cancer. The antibody-boronic acid-metal dioxime complex conjugate is relatively non-reactive with tissue not associated with the tumor or cancer.

Either the complexes of this invention or the proteins or antibodies labeled with the complexes of this invention can be administered to a host by bolus intravenous injection or intraperitoneally. The size of the host, and the imaging system used, will determine the quantity of radioactivity needed to produce diagnostic images. For a human host, the quantity of radioactivity injected will normally range from about 5 to 20 millicuries of technetium-99m.

The above mode of administration is also applicable when the complexes of this invention, by themselves, or when coupled to antibodies or proteins are used in radiotherapy. The quantity of radioactivity in radiotherapy for a human host will range from about 10 to 30 millicuries.

The following examples are specific embodiments of this invention.

EXAMPLE 1 m-Isothiocyanatophenylboronic Acid

To a cooled (0° C.) solution of 3-aminophenylboronic acid (2.24 g, 0.013 mol) in acetone (5 ml) was added dropwise a solution of thiophosgene (1 ml, 0.013 mol) in chloroform (5 ml) over a period of 0.5 hour. The reaction mixture was stirred at 0° C. for 1 hour and at room temperature for 12 hours. The solvent was evaporated on a rotary evaporator and the residue was triturated with ether and filtered to remove the triethylamine hydrochloride. The ether solution was evaporated to a brown oil. This was chromatographed on silica gel (30 g) using acetone-chloroform (7:3) as eluent. Fractions containing the product were collected and evaporated to give a light brown solid. This solid was crystallized from ethyl acetate/hexane. M.P. 166°-67° C. Anal. Calcd. for $C_7H_6NSBO_2O$: C, 46,00; H, 3.59; N, 7.67; S, 17.54. Found: C, 46.17; H, 3.48; N, 7.59; S, 17.71.

EXAMPLE 2

3-Isothiocyanato-5-carboxyphenylboronic Acid

EXAMPLE 2A m-Tolylboronic Acid

A solution of m-bromotoluene (25 g. 0.146 mol) in ether (200 ml) was added dropwise to magnesium (4.0 g, 0.17 mol) in ether (50 ml) at room temperature over a period of 3 hours under a nitrogen atmosphere. After the addition, the reaction mixture was stirred for 12 hours at room temperature. The Grignard reagent was added slowly to a solution of trimethyl borate (15.6 g, 17 ml, 0.15 mol) in ether (500 ml) over a period of 4 hours at −78° C. and stirred for 12 hours at room temperature. The reaction mixture was hydrolyzed with 30% sulfuric acid (50 ml). The ether layer was separated, washed with water (3×250 ml) and dried over $Na_2SO_4$. The solvent was removed on a rotary evaporator and the solid obtained was recrystallized from water. M.P. 160°-161° C.

EXAMPLE 2B m-Carboxyphenylboronic Acid

To a solution of m-Tolylboronic acid (8.0 g, 0.059 mol) in 10% sodium hydroxide (250 ml) was added potassium permanganate (20 g) in small portions. The reaction mixture was stirred at room temperature for 48 hours. The precipitated manganese dioxide was filtered and the filtrate was acidified with 10% sulfuric acid and cooled. The white precipitate that formed was filtered and recrystallized from water. M.P. 250°-52° C.

EXAMPLE 2C

3-Nitro-5-carboxyphenylboronic Acid

To a stirred slurry of m-carboxyphenylboronic acid (5 g, 0.03 mol) in concentrated sulfuric acid (15 ml) was added fuming nitric acid (15 ml, d=1.54). The reaction mixture was stirred at room temperature for 45 minutes and poured on ice (150 g). The nitro acid formed was filtered, washed with water and dried. M.P. 235°-37° C.

EXAMPLE 2D

3-Amino-5-carboxyphenylboronic Acid

A solution of 3-nitro-5-carboxyphenylboronic acid (3.3 g, 0.016 mol) in absolute ethanol (25 ml) was hydrogenated in the presence of Raney Nickel (1 g) at 50 lbs per square inch for 4 hours in a Parr shaker. The catalyst was removed by filtration and the solvent was removed on a rotary evaporator. The solid obtained was recrystallized from water. M.P. 210°-12° C.

EXAMPLE 2E

3-Isothiocyanato-5-carboxyphenylboronic Acid

To a solution of 3-amino-5-carboxyphenylboronic acid (150 mg, 0.08 mmol) in 3N HCl (3 ml) was added thiophosgene (92 mg, 0.08 mmol) in 3N HCl (3 ml) and the reaction mixture was stirred at room temperature. A white solid was formed after 20 minutes. This was recrystallized from hexane/ethyl acetate. M.P. >350° C. Anal. Calcd. for $C_8H_6NO_4BS \cdot 3H_2O$. C, 42.06; H, 2.91; N, 6.13. Found: C, 42.51; H, 2.87; N, 5.68.

EXAMPLE 3 p-Bromomethylbenzeneboronic Acid

EXAMPLE 3a p-Tolylboronic Acid

Into a 200 ml round bottom flask, which had been oven dried and flushed with $N_2$, was added dropwise p-bromotoluene (17.1 g, 0.1 mol in 150 ml of ether) to a mixture of Mg (2.5 g, 0.105 mol) in 30 ml of ether. The reaction mixture was stirred overnight at room temperature. The dark brown solution was then transferred to another addition funnel via a transfer needle, using $N_2$ pressure.

This Grignard reagent was added dropwise over a period of 1.5 hours into a solution of trimethylborate (10.4 g, 0.1 mole) in 200 ml of ether at −78° C. under $N_2$. After stirring overnight at room temperature, this off-white reaction mixture was hydrolyzed with 200 ml of water and acidified with 35 ml of 3N sulfuric acid. The aqueous layer was extracted with ether (4×80 ml). The combined organic layer was washed and dried over $Na_2SO_4$. Removal of solvent yielded a white solid product which was recrystallized from water. M.P. 251°-256° C.

EXAMPLE 3B p-Bromomethylbenzene Boronic Acid

Into a solution of p-tolylboronic acid (2.0 g, $1.47 \times 10^{-2}$ mol) in 40 ml of carbon tetrachloride was added 5 ml of a bromine solution prepared by dissolving 2.4 g of bromine ($1.5 \times 10^{-2}$ mol) in 20 ml of $CCl_4$. The reaction was initiated by illumination with a 150 watt light bulb. The bromine color faded in 5 minutes. The remaining bromine solution was added after 15 minutes. The precipitate that formed was isolated by filtration, and recrystallized from chloroform. M.P. 154°–156° C.

EXAMPLE 4

$^{99m}$Tc(chlorine)(dimethyl glyoxime)$_3$ (3-isothiocyanatophenyl) boron

To a freeze-dried mixture of 2.0 mg of dimethyl glyoxime, 100 mg of sodium chloride, 18 mg of citric acid, 1 mg of diethylenetriamine-penta-acetic acid (DTPA), 50 mg of gammacyclodextrin, and 50 g of stannous chloride in a 5 ml siliconized serum vial was added 3.0 mg of 3-isothiocyanatophenylboronic acid in 50 μl of ethanol.

Sodium pertechnetate in physiological saline (1.0 ml) was added to the vial, which was then heated at 100° C. for 5 minutes. The yield of Tc(chlorine)(dimethyl glyoxime)z(3-isothiocyanatophenyl) boron, as determined by high pressure liquid chromatography (HPLC), was 35–40%. Samples of this complex coelute from Lichrosorb HPLC columns with authentic samples of $^{99}$Tc(chlorine)-(dimethyl glyoxime)$_3$(3-isothiocyanatophenyl) boron that was prepared as described below.

EXAMPLE 4a

$^{99}$Tc(chlorine)(dimethyl glyoxime)$_3$ (3-isothiocyanatophenyl) boron

A solution containing $^{99}$Tc(dimethyl glyoxime)$_3$-(μ—OH)(SnCl$_3$)·3H$_2$O (97 mg, 0.138 mmol), 3-isothiocyanatophenylboronic acid (32 mg, 0.18 mmol), ethanol (10 ml), and 1M HCl (2 ml) was boiled gently in a small beaker for 1 hour in air. The resulting red-orange precipitate (60% yield) was recrystallized from a warm $CH_2Cl_2$/EtOH mixture (1:5). X-Ray structure quality crystals were formed within one day. Anal. (Calcd.) for $C_{19}H_{24}N_7O_6BClSTc$: C, 36.36 (36.59); H, 3.80 (3.89); N, 15.88 (15.72). Molecular ion MH$^+$ observed by mass spectroscopy at m/z=624. Retention time=8.4 minutes on Licrosorb HPLC column (75/25 ACN/0.1M NH$_4$OAc pH 4.6, 1.5 mL/min.) An X-Ray crystal structure determination on this complex confirmed the structure.

EXAMPLE 5

$^{99m}$Tc(chlorine)(dimethyl glyoxime)$_3$ (3-isothiocyanato-5-carboxyphenyl)boron Following the procedure for Example 4, but substituting 3.0 mg of 3-isothiocyanato-5-carboxyphenyl boronic acid for the 3-isothiocyanatophenylboronic acid, yielded 35–40% of the title complex. Samples of this complex coelute from a Nucleosil HPLC column with authentic samples of $^{99}$Tc(chlorine)(dimethyl glyoxime)3(3-isothiocyanato-5-carboxyphenyl) boron prepared as described in 5a below.

EXAMPLE 5a

$^{99}$Tc(chlorine)(dimethyl glyoxime)$_3$ (3-isothiocyanato-5-carboxyphenyl)boron To the complex Tc(chlorine)(dimethyl glyoxime)$_3$ [TcCl(DMG$_3$)] (23.8 mg, 0.049 mmol) in 3 ml of CH$_3$CN was added 3 drops of 1M HCl and 11.5 mg (0.051 mmol) of 3-isothiocyanato-5-carboxyphenyl boronic acid. The reaction mixture was heated at 50° C. with stirring for 15 minutes. It was then treated with an equal volume of 1M HCl and cooled to room temperature. The resulting red-orange precipitate was recrystallized from CH$_3$CN/1M HCl to yield analytically pure needles (75.5% yield), isolated as the 1.5 H$_2$O hydrate. Anal. (Calcd.) for $C_{20}H_{24}N_7BClO_8STc \cdot 1.5$ H$_2$O: C, 34.76 (34.57); H, 3.90 (3.92); N, 13.90 (14.11). Retention time=2.85 min., Nucleosil HPLC column (65/35 ACN/0.1M citric acid, 1.5 ml/min.).

EXAMPLE 6

$^{99m}$Tc(chlorine)(1,2-cyclohexanedione dioxime)$_3$ (3-isothiocyanatophenyl)boron To a freeze-dried mixture of 1.5 mg of 1,2-cyclohexanedionedioxime, 100 mg of sodium chloride, 9 mg of citric acid, 2 mg of diethyl-enetriamine-penta-acetic acid (DTPA), 50 mg of gamma-cyclodextrin, and 50 μg of stannous chloride in a 5 ml siliconized serum vial was added 2.4 mg of 3-isothiocyanatophenylboronic acid in 50 μl of ethanol.

Sodium pertechnetate in physiological saline (1.0 ml) was added to the vial, which was then heated at 100° C. for 15 minutes. The yield of Tc(chlorine) (1,2 cyclohexanedione dioxime)$_3$(3-isothiocyanatophenyl) boron, as determined by high pressure liquid chromatography (HPLC), was 33%. Samples of this complex coelute from Licrosorb HPLC columns with authentic samples of a $^{99}$Tc standard, prepared as described in 6a below.

EXAMPLE 6a

$^{99}$Tc(chlorine)(1,2-cyclohexanedione dioxime)$_3$ (3-isothiocyanatophenyl)boron A solution containing $^{99}$Tc(1,2-cyclohexanedione dioxime)$_3$(μ—OH)SnCl$_3$·3H$_2$O (77 mg, 0.095 mmol), 3-isothiocyanatophenylboronic acid (22 mg, 0.12 mmol), ethanol (10 ml), and 1M HCl (2 ml) was boiled in a small beaker for 1 hour in air. During this time, the volume of the solution reduced to 2 ml, and orange crystals of product precipitated (66% yield). The product was purified on a silica gel column; elution with 5% ACN/95% CH$_2$Cl$_2$ yielded analytically pure product upon evaporation of solvent. Anal. (Calcd.) for $C_{25}H_{30}N_7BClO_6STc$: C, 42.65 (42.78); H, 4.44 (4.31); N, 14.26 (13.87). Samples of this complex eluted from Licrosorb HPLC columns at a retention time of 8 minutes (90/10 ACN/0.1M NH$_4$OAc pH 4.6, 1.5 ml/min.).

EXAMPLE 7

$^{99m}$Tc(chlorine) (1,2-cyclohexanedione dioxime)$_3$(3-isothiocyanato-5-carboxyphenyl)boron Following the procedure of Example 6, but substituting 3.0 mg of 3-isothiocyanato-5-carboxyphenylboronic acid for the 3-isothiocyanatophenylboronic acid, yielded 35% of the title complex. Samples of this complex eluted from Nucleosil HPLC columns at a retention time identical to that of a $^{99}$Tc standard of the title complex, prepared as described in Example 12a.

EXAMPLE 8

$^{99m}$Tc(chlorine) (dimethyl glyoxime)$_3$

Following the procedure of example 4, but omitting the boronic acid entirely, and heating the kit for 2.5 minutes at 100° C., the complex $^{99m}$TC(chlorine) (dimethyl glyoxime)$_3$ was prepared in 76% yield.

EXAMPLE 9

$^{99m}$Tc(chlorine) (dimethyl glyoxime)$_3$(3-isothiocyanato-5-carboxyphenyl)boron To 99mTc(chlorine) (dimethyl glyoxime)$_3$ prepared as described in Example 8, was added 3.0 mg of 3-isothiocyanato-5-carboxyphenylboronic acid in 50 μl of ethanol. The mixture was heated at 100° C. for 5 minutes yielding the title compound in 62% yield. Samples of this complex coeluted from Nucleosil HPLC columns at a retention time identical to that of an authentic $^{99}$Tc standard of the complex, prepared as described in Example 5a.

EXAMPLE 10

$^{99m}$Tc(chlorine) (1,2-cyclohexanedione dioxime)$_3$

Following the procedure of Example 6, but omitting the boronic acid entirely, the yield of $^{99m}$Tc(chlorine)(1,2-cyclohexanedionedioxime)$_3$ was 92%.

EXAMPLE 11

$^{99m}$Tc(chlorine) (1,2-cyclohexanedione dioxime)$_3$(3-isothiocyanatophenyl)boron To $^{99m}$Tc(chlorine) (1,2-cyclohexanedione (dioxime)$_3$ prepared as described in Example 10, was added 2.4 mg of 3-isothiocyanatophenylboronic acid in 50 μl of ethanol. The mixture was heated for 15 minutes at 100° C. The yield of title complex, prepared by this route, was 48.5%. Samples of this complex coeluted from Licrosorb HPLC columns at a retention time identical to that of an authentic $^{99}$Tc standard that was prepared as described in Example 6a.

EXAMPLE 12

$^{99m}$Tc(chlorine) (1,2-cyclohexanedione dioxime)$_3$ (3-isothiocyanato-5-carboxyphenyl)boron A sample of $^{99m}$Tc(chlorine) (1,2-cyclohexanedione dioxime)$_3$ was prepared as described in Example 10. The complex was isolated, and kit components were removed, by purification on Hamilton PRP-1 resin, as follows. The kit contents were drawn up into a needle-hub containing the resin and then rinsed with 1 ml of saline, 1 ml of 25/75 EtOH/saline, 1 ml of H$_2$O, and 1 ml of EtOH.

An 0.5 ml aliquot of the ethanol fraction, which contained purified $^{99m}$Tc(chlorine) (1,2cyclohexanedione dioxime)$_3$ was added to a vial that contained 1.5 mg of 3-isothiocyanato-5-carboxyphenyl)boron and 50 μl of 1N HCl. This kit was heated for 5 minutes at 100° C. This procedure gave the title complex in 81.7% yield. Samples of this complex co-eluted from HPLC columns at the retention time of an authentic $^{99}$Tc standard of the complex that was prepared as described in 12a below.

EXAMPLE 12a $^{99}$Tc(chlorine) (1,2-cyclohexanedione dioxime)$_3$ (3-isothiocyanato-5-carboxyphenyl)boron To 4.0 mg of $^{99}$Tc(chlorine) (1,2-cyclohexanedione dioxime)$_3$, dissolved in 3 ml of ACN was added 1.5 mg of 3-isothiooyanato-5-carboxyphenyl boronic acid and 3 drops of 3M HCl. The solution was heated gently for 20 minutes. The complex $^{99}$Tc(chlorine)(1,2-cyclohexanedione)a(3-isothiocyanato-5-carboxyphenyl)boron was formed in quantitative yield. Samples of this complex gave a strong molecular ion peak MH+ by fast atom bombardment mass spectroscopy and had a retention time of 8.0 minutes on Nucleosil HPLC columns (ACN/0.1M citric acid 60/40, 1.5 ml/min.).

EXAMPLE 13

$^{99m}$Tc(chlorine) (dimethyl glyoxime)$_3$-p-bromomethylphenyl) boron

To a freeze-dried mixture of 2.0 mg of dimethyl glyoxime, 100 mg of sodium chloride, 18 mg of citric acid, 1 mg of diethylenetriamine-penta-acetic acid (DTPA), 50 mg of gammacyclodextrin, and 50 μg of stannous chloride in a 5 ml siliconized serum vial was added 2.0 mg of p-bromomethylphenyl boronic acid (OH)$_2$BPh—CH$_2$Br.

Sodium pertechnetate in physiological saline (0.25 ml) was added to the vial, followed by 1.0 ml of methanol. The kit was heated at 100° C. for 10 minutes. The yield of Tc(chlorine) (dimethyl glyoxime)$_3$ (4-bromomethylphenyl)boron, as determined by high pressure liquid chromatography (HPLC), was 5.7%.

EXAMPLE 14

Labeling of glycine with $^{99m}$Tc(chlorine)(dimethyl glyoxime)$_3$(3-isothiocyanatophenyl)-boron (Tc-DMG-BPITC)

A solution of $^{99m}$Tc(chlorine) (dimethyl glyoxime)$_3$(3-isothiocyanatophenyl)boron (Tc-DMG-BPITC) prepared as described in Example 4, was purified by adsorption onto Reverse Phase resin (as in Example 12). After washing the resin with 50% ethanol/50% normal saline to remove impurities and excess boronic acid, the desired complex was eluted from the resin with ethanol. A 200 μl aliquot of this ethanol solution was mixed with 200 μl of glycine (20 mg/mL in 0.1M sodium phosphate buffer pH 9.0). The mixture was incubated at 37° C. for 1 hour. Analysis of the reaction by HPLC showed that all starting material had disappeared at this time. The yield of Tc-labeled glycine (Tc-DMG-BPITC-Glycine) was 88%, as determined by HPLC.

EXAMPLE 15

Labeling of polylysine with $^{99m}$Tc-DMG-BPITC

A sample of Tc(chlorine) (dimethyl glyoxime)$_3$ (3-isothiocyanatophenyl)boron(Tc-DMG-BPITC), prepared as described in Example 4, and purified as described in Example 14, was evaporated to dryness with a nitrogen stream. The complex was re-dissolved in 50 μl of DMSO, and 10 μl of this DMSO solution was added to 100 μl of pH 9.0 0.1M sodium phosphate buffer that contained 0.5 mg of polylysine (average m.w.=102,000). After incubation at 37° C. for 2 hours, the yield of Tc-labelled polylysine (Tc-DMG-BPITCpolylysine) was 36%, as estimated by HPLC on a Pinkerton ISRP column.

EXAMPLE 16

Labeling of mouse IgG with $^{99m}$Tc-DMG-BPITC

A sample of Tc(chlorine) (dimethyl glyoxime)$_3$-(3-isothiocyanatophenyl)boron (Tc-DMG-BPITC), prepared as described in Example 4, and purified as described in Example 14, was evaporated to dryness with a nitrogen stream. The complex was re-dissolved in 50 μl of DMSO, and 10 μl of this DMSO solution was added to 100 μl of pH 9.5 0.1M sodium phosphate buffer that contained 0.5 mg of mouse IgG. After incubation at 37° C. for 2.5 hours, the yield of Tc-labeled mouse IgG was 34%, as estimated by HPLC on a Pinkerton ISRP column.

EXAMPLE 17

Labeling of the Monoclonal Antibody B72.3 With $^{99m}$Tc-DMG-BPITC

A sample of Tc(chlorine) (dimethyl glyoxime)$_3$ (3-isothiocyanatophenyl)boron (Tc-DMG-BPITC), prepared as described in Example 4, and purified as described in Example 14, was evaporated to dryness with a nitrogen stream. The complex was re-dissolved in 50 μl of DMSO, and 10 μl of this DMSO solution was added to 100 μl of pH 9.5 0.1M sodium phosphate buffer that contained 1.0 mg of antibody B72.3. This antibody is described by D. Colcher et al., Nucl. Med. Biol., Vol. 14 (3) p. 251-262 (1987). After incubation at 37° C. for 2.0 hours, the yield of Tc-labeled B72.3 was 10%, as estimated by HPLC on an ISRP-TSK column.

EXAMPLE 18

Labeling of the Monoclonal Antibody B72.3 with $^{99m}$Tc-DMG-NCS-COOH

A sample of Tc(chlorine) (dimethyl glyoxime)$_3$-(3-carboxy-5-isothiocyanatophenyl)boron (Tc-DMG-NCS-COOH), prepared as described in Example 5, and purified as described in Example 14, was evaporated to dryness with a nitrogen stream. The complex was re-dissolved in 100 μl of pH 9.5 0.1M sodium phosphate buffer that contained 1.0 mg of B72.3. After incubation at 37° C. for 2.0 hours, the yield of Tc-labeled B72.3 was 34%, as estimated by HPLC on an ISRP-TSK column.

EXAMPLE 19

Affinity Chromatography of the Monoclonal Antibody B72.3 Labelled with $^{99m}$Tc-DMG-NCS-COOH A sample of $^{99m}$Technetium labelled B72.3, prepared as described in Example 18, was purified from excess labelling reagent by passage through an ISRP and TSK column, linked in series. An aliquot of the purified antibody (about 50,000 cpm/128 ng of protein) was loaded onto a TAG-72 affinity column and incubated at room temperature. The column was washed with PBS buffer to elute non-specifically bound protein. The active labelled antibody was then eluted from the column with 6M guanidine. The immunoreactivity of the antibody, expressed as a percentage, is defined as [(activity in cpm eluted with guanidine/total activity in cpm eluted from the column)×100]. An immunoreactivity of 72% was seen. For comparison, a sample of B72.3 labeled by standard methods with $^{125}$Iodine was 55-60% immunoreactive, as assayed using a TAG-72 affinity column.

EXAMPLE 20

Biodistribution of $^{99m}$Tc-labeled B72.3 in Tumor-bearing mice

Tumor-bearing (GW39 tumor line) nude mice were injected with 10-20 uCi of Tc-labelled B72.3 prepared as described in Example 18 and purified by HPLC as described in Example 19. The animals were sacrificed at 2 or 24 hours (n=5 animals for each time point), and organs of interest dissected and counted for radioactivity. For comparison, $^{131}$Iodine labelled B72.3 was injected into a control set of tumor-bearing mice. Data from this experiment (enclosed as Table 1), indicated specific localization of both the Iodine and Tc-labelled B72.3 in the tumors.

EXAMPLE 21

Labeling of the Monoclonal Antibody NP-4 With $^{99m}$Tc-DMG-NCS-COOH

A sample of Tc(chlorine)(dimethyl glyoxime)$_3$-(3-carboxy-5-isothiocyanatophenyl)boron (Tc-DMG-NCS-COOH), prepared as described in Example 5, and purified as described in Example 14, was evaporated to dryness with a nitrogen stream. The complex was re-dissolved in 100 μl of pH 9.5 0.1M sodium phosphate buffer that contained 1.0 mg of NP-4(CMMI, Newark, New Jersey). After incubation at 37° C. for 2.0 hours, the yield of Tc-labeled NP-4 was 40%, as estimated by HPLC on an ISRP-TSK column.

EXAMPLE 22

Affinity Chromatography of the Monoclonal Antibody NP-4 Labelled With $^{99m}$Tc-DMG-NCS-COOH A sample of $^{99m}$Technetium labelled NP-4, prepared as described in Example 21, was purified from excess labelling reagent by passage through an ISRP-TSK HPLC column. An aliquot of the purified antibody (about 50,000 cpm/128 ng of protein) was loaded onto an anti-CEA affinity column and incubated at room temperature. The column was washed with PBS buffer to elute non-specifically bound protein. The active labelled antibody was then eluted from the column with 6M quanidine. The immunoreactivity of the antibody, expressed as a percentage, is defined as [(activity in cpm eluted with guanidine/total activity in cpm eluted from the column)×100]. An immunoreactivity of 95.8% was seen.

EXAMPLE 23

Biodistribution of $^{99m}$Tc-labeled NP-4 in Tumor-Bearing Mice

Tumor-bearing (GW39 tumor line) nude mice were injected with 50 μCi of Tc-labelled NP-4 prepared as described in Example 21 and purified by HPLC as described in Example 22. The animals were sacrificed at 2 or 24 hours (n=6 animals for each time point), and organs of interest dissected and counted for radioactivity. Data from this experiment (enclosed as Table 2), indicated specific localization of the $^{99m}$-Tc-labelled NP-4 in the tumors. At 24 hours, an average of 16.56% of the injected dose was seen per gram of tumor.

EXAMPLE 24

Labeling of the Monoclonal Antibody F(ab')2 Fragment of NP-4 with $^{99m}$Tc-DMG-NCS-COOH A sample of Tc(chlorine)(dimethyl glyoxime)3-(3-carboxy-5-isothiocyanatophenyl)boron (Tc-DMG-NCSCOOH), prepared as described in Example 5, and purified as described in Example 14, was evaporated to dryness with a nitrogen stream. The complex was redissolved in 100 μl of pH 9.5, 0.1M sodium phosphate buffer that contained 1.0 mg of the F(ab')2 fragment of NP-4 (CMMI, Newark, New Jersey). After incubation at 37° C. for 2.0 hours, the yield of Tc-labeled NP-4-F(ab')2 was 15.2%, as estimated by HPLC on an ISRP-TSK column.

EXAMPLE 25

Affinity Chromatography of the Monoclonal Antibody F(ab')2 fragment of NP-4 Labelled with $^{99m}$Tc-DMG-NCS-COOH A sample of $^{99m}$Technetium labelled NP-4-F(ab')2, prepared as described in Example 24, was purified from excess labelling reagent by passage through an ISRP-TSK HPLC column. An aliquot of the purified antibody (about 30,000 cpm/100 ng of protein) was loaded onto an anti-CEA affinity column and incubated at room temperature. The column was then washed with PBS buffer to elute non specifically bound protein. The active labelled antibody fragment was then eluted from the column with 6M guanidine. The immunoreactivity of the antibody, expressed as a percentage, is defined as [(activity in cpm eluted with guanidine/total activity in cpm eluted from the column) × 100]. An average immunoreactivity of 94% was seen.

EXAMPLE 26

Biodistribution of $^{99m}$Tc-labelled NP-4F(ab')2 Fragment in Tumor-Bearing Mice Tumor-bearing (GW39 tumor line) nude mice were injected with 20-30 μCi of Tc-labelled F(ab')2 fragment of NP-4 prepared as described in Example 24 and purified by HPLC as described in Example 25. The animals were sacrificed at 2 or 24 hours (n=6 animals for each time point), and organs of interest dissected and counted for radioactivity. Data from this experiment (enclosed as Table 3), indicated specific localization of the $^{99m}$-Tc-labelled NP-4F(ab')2 fragment in the tumors. At 24 hours, an average of 10.5% of the injected dose was seen per gram of tumor.

EXAMPLE 27

Labeling of the Monoclonal Antibody B72.3 With Tc(chlorine)(1,2-cyclohexanedione dioxime)3-(3-isothiocyanato-5-carboxyphenyl)boron A sample of $^{99m}$Tc(chlorine)(1,2-cyclohexanedione dioxime)3 (3-isothiocyanato-5-carboxyphenyl) boron was prepared as described in Example 12, diluted to 2 ml with normal saline, purified as described in Example 14, and evaporated to dryness with a nitrogen stream. The complex was redissolved in 100 μl of pH 9.5 0.1M sodium phosphate buffer that contained 1.0 mg of the monoclonal antibody B72.3. After incubation at 37° C. for 2 hours, the yield of $^{99m}$Tc-labeled B72.3 was 7.4%, as estimated by HPLC on an ISRP-TSK column.

TABLE 1

Comparison of the biodistribution of $^{99m}$Tc and $^{131}$I labeled B72.3 in Tumor (GW39) bearing nude mice.

| Tissue | injected dose/gram tissue | |
|---|---|---|
| | 2 hr p.i. | 24 hr p.i. |
| a. $^{99m}$Tc-B72.3 (from example 18) | | |
| GW39 | 2.48 ± 0.749 | 10.47 ± 3.788 |
| Liver | 9.05 ± 0.719 | 6.13 ± 1.227 |
| Spleen | 7.70 ± 1.079 | 3.82 ± 1.098 |
| L. Kidney | 10.49 ± 3.701 | 5.17 ± 0.866 |
| Lungs | 14.47 ± 4.684 | 8.30 ± 1.984 |
| Blood | 30.66 ± 3.362 | 15.84 ± 2.255 |
| Urine | 7.88 ± 0.900 | 6.50 ± 3.640 |
| Stomach | 2.51 ± 1.950 | 1.60 ± 0.343 |
| Small Int. | 4.47 ± 0.522 | 3.31 ± 0.298 |
| Muscle | 1.37 ± 0.243 | 1.46 ± 0.320 |
| Bone | 2.91 ± 0.586 | 1.91 ± 0.414 |
| b. $^{131}$I-B72.3 | | |
| GW39 | 3.10 ± 1.411 | 18.20 ± 8.362 |
| Liver | 7.80 ± 1.166 | 5.50 ± 1.129 |
| Spleen | 8.57 ± 3.169 | 5.11 ± 1.508 |
| L. Kidney | 11.19 ± 6.655 | 6.26 ± 1.027 |
| Lungs | 12.48 ± 1.577 | 8.46 ± 1.209 |
| Blood | 25.96 ± 7.317 | 18.98 ± 2.708 |
| Urine | 8.45 ± 4.887 | 4.28 ± 1.701 |
| Stomach | 2.46 ± 0.717 | 4.47 ± 1.123 |
| Small Int. | 2.04 ± 0.426 | 1.45 ± 0.176 |
| Muscle | 1.33 ± 0.435 | 2.16 ± 0.315 |
| Bone | 3.43 ± 1.212 | 2.63 ± 0.475 |

TABLE 2

The biodistribution of $^{99m}$Tc-NP-4 whole antibody in Tumor (GW39) bearing nude mice.

| Tissue | injected dose/gram tissue | |
|---|---|---|
| | 2 hr p.i. | 24 hr p.i. |
| GW39 | 1.75 ± 0.783 | 16.56 ± 5.822 |
| Liver | 5.79 ± 1.234 | 4.29 ± 0.365 |
| Spleen | 4.74 ± 0.935 | 3.86 ± 1.104 |
| L. Kidney | 7.14 ± 1.463 | 3.51 ± 0.709 |
| Lungs | 10.45 ± 1.849 | 5.43 ± 1.795 |
| Blood | 20.97 ± 3.594 | 11.46 ± 1.286 |
| Urine | 5.36 ± 0.712 | 7.05 ± 2.641 |
| Stomach | 1.35 ± 0.338 | 1.51 ± 0.458 |
| Small Int. | 1.62 ± 0.392 | 2.06 ± 0.409 |
| Muscle | 0.92 ± 0.240 | 1.37 ± 0.239 |
| Bone | 2.75 ± 0.740 | 1.92 ± 0.490 |

TABLE 3

The biodistribution of $^{99m}$Tc-NP-4 F(ab')2 in Tumor (GW39) bearing nude mice.

| Tissue | injected dose/gram tissue | |
|---|---|---|
| | 2 hr p.i. | 24 hr p.i. |
| GW39 | 3.99 ± 0.578 | 10.47 ± 2.595 |
| Liver | 8.01 ± 2.383 | 4.16 ± 1.530 |
| Spleen | 6.22 ± 2.466 | 3.26 ± 2.398 |
| L. Kidney | 17.66 ± 5.709 | 17.95 ± 10.516 |
| Lungs | 10.87 ± 3.409 | 3.78 ± 1.785 |
| Blood | 29.37 ± 7.068 | 6.24 ± 2.122 |
| Urine | 28.24 ± 12.850 | 11.73 ± 9.797 |
| Stomach | 2.79 ± 0.545 | 0.71 ± 0.328 |
| Large Int. | 3.72 ± 0.543 | 3.15 ± 1.208 |
| Muscle | 1.30 ± 0.198 | 1.13 ± 0.508 |
| Bone | 4.32 ± 2.320 | 1.73 ± 0.829 |

What is claimed is:

1. Boronic acid adducts of Metal dioxime complexes having the formula $$MX(Y)_3Z \qquad \qquad 1$$

wherein:

M is an isotope of technetium or rhenium,

X is an anion,
Y is a vicinal dioxime having the formula

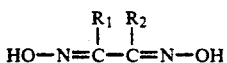

or a pharmaceutically acceptable salt thereof, and $R_1$ and $R_2$ are each independently hydrogen, halogen, alkyl, aryl or a 5 or 6-membered nitrogen, sulfur or oxygen containing heterocycle, or together $R_1$ and $R_2$ are $-(CR_8R_9)_n-$ wherein n is 3, 4, 5 or 6 and $R_8$ and $R_9$ are each independently hydrogen or alkyl; and
Z is a boron derivative having the formula

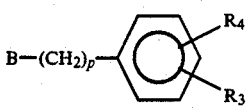

wherein P is zero or an integer from one to six, $R_3$ is NCS, and $R_4$ is hydrogen, or a water solubilizing functionality selected from the group consisting of COOH, carboxyalkyl, hydroxyalkyl, $SO_3H$, alkylsulfonate, sulphonamide, or hydroxyl, or a pharmaceutically acceptable salt thereof.

2. A complex according to claim 1 wherein $R_4$ is meta to $R_3$.

3. A complex according to claim 1 wherein $R_4$ is meta to the spacer group $(A_1)_p$.

4. A boronic acid adduct in accordance with claim 1, wherein M is an isotope of technetium.

5. A boronic acid adduct in accordance with claim 1, wherein M is an isotope of rhenium.

6. A boronic acid adduct in accordance with claim 1, wherein X is chloride or hydroxide.

7. A boronic acid adduct in accordance with claim 1, wherein X is chloride.

8. A boronic acid adduct in accordance with claim 1, wherein Y is dimethyl glyoxime, 1,2-ethanedione dioxime, 1,2-cyclopentanedione dioxime or 1,2-cyclohexanedione dioxime.

9. A boronic acid adduct in accordance with claim 1, wherein Y is dimethyl glyoxime.

10. A boronic acid adduct in accordance with claim 1, wherein Y is 1,2-cyclohexanedione dioxime.

11. A boronic acid adduct in accordance with claim 1, wherein Z is 3-isothiocyanatophenylboron.

12. A boronic acid adduct in accordance with claim 1, wherein Z is 4-isothiocyanatophenylboron.

13. A boronic acid adduct in accordance with claim 1, wherein Z is 3-carboxy-5-isothiocyanatophenylboron.

14. A boronic acid adduct in accordance with claim 1, wherein $R_4$ is COOH, or $SO_3H$ or a pharmaceutically acceptable salt thereof.

15. A boronic acid adduct in accordance with claim 1, wherein $R_4$ is COOH or a pharmaceutically acceptable salt thereof.

16. The boronic acid adduct in accordance with claim 1, Tc(chlorine) (1,2-cyclohexane-dione)$_3$ (3-carboxy-5-isothiocyanatophenylboron).

17. The boronic acid adduct in accordance with claim 1, Tc(chlorine) (1,2-cyclohexane-dione)$_3$ (3-isothiocyanatophenylboron).

18. The boronic acid adduct in accordance with claim 1, Re(chlorine) (1,2-cyclohexane-dione)$_3$ (3-isothiocyanatophenylboron).

19. The boronic acid adduct in accordance with claim 1, Re(chlorine) (1,2-cyclohexane-dione)$_3$ (3-carboxy-5-isothiocyanatophenylboron).

20. The boronic acid adduct in accordance with claim 1, Tc(chlorine) (dimethyl glyoxime)$_3$ (3-isothiocyanatophenylboron).

21. The boronic acid adduct in accordance with claim 1, Tc(chlorine) (dimethyl glyoxime)$_3$ (3-carboxy-5-isothiocyanatophenylboron).

22. The boronic acid adduct in accordance with claim 1, Re(chlorine) (dimethylglyoxime)$_3$ (3-isothiocyanatophenylboron).

23. The boronic acid adduct in accordance with claim 1, Re(chlorine) (dimethyl glyoxime)$_3$ (3-carboxy-5-isothiocyanatophenylboron).

24. An antibody-metal dioxime complex conjugate, said conjugate being formed by reaction of the boronic acid adducts of metal dioxime compounds of claim 1, with antibodies or antibody fragments.

25. An antibody-metal dioxime complex conjugate according to claim 24, wherein the antibody fragment is selected from the group consisting of Fab fragments, (Fab')$_2$ fragments and Fab' fragments.

26. An antibody-metal dioxime-complex conjugate according to claim 24, wherein the antibody or antibody fragment is a monoclonal antibody or monoclonal antibody fragment.

27. A protein-metal dioxime complex conjugate, said conjugate being formed by reaction of the boronic acid adducts of metal dioxime compounds of claim 1, with a protein.

28. A protein-metal dioxime complex conjugate according to claim 27, wherein the protein is selected from the group consisting of fibrinogen, fibrin, and low density lipoprotein.

29. A method for the diagnosis of cancer, comprising the administration of an antibody-boronic acid-radioactive metal-dioxime complex conjugate according to claim 24, said conjugate being immunoreactive with and immunospecific for a target site associated with the cancer, and relatively non reactive with tissues not associated with the disorder.

30. A method for the diagnosis of cancer, comprising the administration of an antibody fragment-boronic acid-metal dioxime complex conjugate according to claim 25, said conjugate being immunoreactive with and immunospecific for a target site associated with the cancer, and relatively non-reactive with tissues not associated with the disorder.

31. A method for the therapeutic treatment of cancer, said method comprising the administration of a therapeutically effective amount of an antibody-boronic acid-metal dioxime complex conjugate, according to claim 24, said conjugate being immunoreactive with and immunospecific for a target site associated with the cancer, and relatively non reactive with tissues not associated with the disorder.

32. A method for the therapeutic treatment of cancer, said method comprising the administration of a therapeutically effective amount of an antibody fragment-boronic acid-metal dioxime complex conjugate, according to claim 25, said conjugate being immunoreactive with and immunospecific for a target site associated with the cancer, and relatively non reactive with tissues not associated with the disorder.

* * * * *